(12) United States Patent
Takahashi et al.

(10) Patent No.: US 9,101,513 B2
(45) Date of Patent: Aug. 11, 2015

(54) DISPOSABLE DIAPER

(75) Inventors: Yuki Takahashi, Mima-gun (JP); Emi Amano, Mima-gun (KE); Kenji Nakaoka, Osaka (JP)

(73) Assignee: LIVEDO CORPORATION, Ehime (JP)

( * ) Notice: Subject to any disclaimer, the term of this patent is extended or adjusted under 35 U.S.C. 154(b) by 194 days.

(21) Appl. No.: 13/807,974

(22) PCT Filed: Jun. 20, 2011

(86) PCT No.: PCT/JP2011/003501
§ 371 (c)(1),
(2), (4) Date: Jan. 2, 2013

(87) PCT Pub. No.: WO2012/004941
PCT Pub. Date: Jan. 12, 2012

(65) Prior Publication Data
US 2013/0110065 A1    May 2, 2013

(30) Foreign Application Priority Data

Jul. 5, 2010  (JP) .................................. 2010-152671

(51) Int. Cl.
*A61F 13/15*     (2006.01)
*A61F 13/20*     (2006.01)
(Continued)

(52) U.S. Cl.
CPC ......... *A61F 13/15699* (2013.01); *A61F 13/496* (2013.01); *A61F 13/49466* (2013.01);
(Continued)

(58) Field of Classification Search
CPC ............ A61F 13/15699; A61F 13/496; A61F 13/51498; A61F 13/539; A61F 2013/51007
USPC .................................................. 604/365, 384
See application file for complete search history.

(56) References Cited

U.S. PATENT DOCUMENTS

| | | | |
|---|---|---|---|
| 4,815,660 | A | 3/1989 | Boger |
| 5,858,012 | A | 1/1999 | Yamaki et al. |

(Continued)

FOREIGN PATENT DOCUMENTS

| | | |
|---|---|---|
| CN | 1183946 | 6/1998 |
| EP | 1 621 168 | 2/2006 |

(Continued)

OTHER PUBLICATIONS

International Search Report issued Nov. 8, 2011 in International (PCT) Application No. PCT/JP2011/003501.

(Continued)

*Primary Examiner* — Melanie Hand
*Assistant Examiner* — Aundria Hairell
(74) *Attorney, Agent, or Firm* — Wenderoth, Lind & Ponack, L.L.P.

(57) ABSTRACT

In a pants-type disposable diaper, an outer covering sheet formed of a nonwoven fabric has front and back parts to be positioned on front and back sides of a wearer, and a middle part between the front and back sides. An absorbent body is attached on the outer covering sheet from the front part to the back part, to absorb excrement from the wearer. Sheet members are bonded on the front and back parts, and end portions of the absorbent body are positioned and fixed between the sheet members and the outer covering sheet. In the disposable diaper, since the sheet member is a laminated sheet of plastic film and nonwoven fabric, stretching of the sheet member is suppressed and it is possible to bring the absorbent body in close contact with the crotch region of the wearer when putting the disposable diaper on the wearer.

6 Claims, 4 Drawing Sheets

(51) Int. Cl.
*A61F 13/494* (2006.01)
*A61F 13/514* (2006.01)
*A61F 13/515* (2006.01)
*A61F 13/539* (2006.01)
*A61F 13/496* (2006.01)
*A61F 13/51* (2006.01)

(52) U.S. Cl.
CPC ......... *A61F13/515* (2013.01); *A61F 13/51498* (2013.01); *A61F 13/539* (2013.01); *A61F 2013/51007* (2013.01)

(56) References Cited

U.S. PATENT DOCUMENTS

| | | | |
|---|---|---|---|
| 6,464,677 | B1 | 10/2002 | Noguchi et al. |
| 6,624,340 | B2 | 9/2003 | Mizutani et al. |
| 7,160,408 | B2* | 1/2007 | Otsubo .................. 156/163 |
| 7,686,795 | B2 | 3/2010 | Ichikawa et al. |
| 2004/0186453 | A1 | 9/2004 | Shimada et al. |
| 2005/0137549 | A1 | 6/2005 | Lindsay et al. |
| 2006/0025746 | A1 | 2/2006 | Sasaki et al. |
| 2008/0228158 | A1 | 9/2008 | Sue et al. |
| 2009/0030392 | A1 | 1/2009 | Kanai et al. |
| 2010/0076394 | A1* | 3/2010 | Hayase et al. ........... 604/385.29 |

FOREIGN PATENT DOCUMENTS

| | | |
|---|---|---|
| JP | 2-69906 | 5/1990 |
| JP | 07-054244 Y * | 12/1995 |
| JP | 8-280739 | 10/1996 |
| JP | 9-313533 | 12/1997 |
| JP | 2001-61885 | 3/2001 |
| JP | 2005-237768 | 9/2005 |
| JP | 2006-61682 | 3/2006 |
| JP | 2006-247009 | 9/2006 |
| JP | 2007-097979 | 4/2007 |
| JP | 2008-212232 | 9/2008 |
| JP | 2008-228835 | 10/2008 |
| KR | 10-0699765 | 3/2007 |
| KR | 10-0705184 | 4/2007 |

OTHER PUBLICATIONS

Patent Cooperation Treaty (PCT) Written Opinion of the International Searching Authority issued Nov. 8, 2011 in International (PCT) Application No. PCT/JP2011/003501.

* cited by examiner

DISPOSABLE DIAPER

BACKGROUND OF THE INVENTION

1. Technical Field

The present invention relates to a pants-type disposable diaper.

2. Description of the Related Art

A pants-type disposable diaper which has a waist opening at an upper end and a pair of leg openings on a lower part is conventionally used as one type of absorbent product for receiving excrement from a wearer. Such a disposable diaper has an outer covering sheet where a front part and a back part, to be positioned on a front side and a back side of a wearer, are continuous with each other via a middle part, and left and right ends of the front part are bonded to left and right ends of the back part, respectively, to form a waist opening and a pair of leg openings. In addition, an absorbent body to absorb excrement from the wearer is attached on the outer covering sheet so as to lie from the front part to the back part.

In Japanese Patent Application Laid-Open No. 2007-97979, a pair of end holding sheets which is bonded to a front part and a back part, respectively to cover both end portions of an absorbent body in a longitudinal direction is disclosed, and the absorbent body is securely fixed on an outer covering sheet by the end holding sheets.

Recently, comfort level of wearing a disposable diaper is progressively improved by thinning and softening of its outer covering sheet which is made of a nonwoven fabric; however, the outer covering sheet of such disposable diaper is easily stretched. Thus, when the disposable diaper is put on a wearer, even if the front part and the back part are pulled up in order to bring the absorbent body in close contact with the crotch region of the wearer, it is not easy to pull up the absorbent body itself because of stretching of the outer covering sheet. When the absorbent body is not in close contact with the crotch region of the wearer, there may be a case where excrement is not absorbed into the absorbent body appropriately and it leaks out to the outside.

SUMMARY OF THE INVENTION

The present invention is intended for a pants-type disposable diaper which has a waist opening at an upper end and a pair of leg openings on a lower part. It is an object of the present invention to easily bring an absorbent body in close contact with a crotch region of a wearer when putting the disposable diaper on the wearer.

A preferred disposable diaper according to the present invention comprises: an outer covering sheet which is folded in a middle part lying between a front part and a back part, the front part and the back part being to be positioned on a front side and a back side of a wearer, left and right ends of the front part being bonded to left and right ends of the back part, respectively, to form a waist opening at upper ends of the front part and the back part and form a pair of leg openings under the front part and the back part, the pair of leg openings lying in left and right of the middle part; an absorbent body which is attached on the outer covering sheet to absorb excrement from the wearer, the absorbent body lying from the front part to the back part; and a sheet member which extends along an edge of upper end in one part of the front part and the back part and which is bonded on an inner surface of the outer covering sheet in the one part, one end portion of the absorbent body being fixed between the sheet member and the outer covering sheet; wherein the outer covering sheet is formed of a nonwoven fabric, the sheet member is a laminated sheet of a plastic film and a nonwoven fabric, and a surface of the sheet member to face the wearer is a surface of the nonwoven fabric. It is therefore possible to easily bring the absorbent body in close contact with the crotch region of the wearer when putting the disposable diaper on the wearer. In addition, moisture of excrement can be prevented from passing through the sheet member to leak out to the outside.

Another preferred disposable diaper according to the present invention comprises: an outer covering sheet which is folded in a middle part lying between a front part and a back part, the front part and the back part being to be positioned on a front side and a back side of a wearer, left and right ends of the front part being bonded to left and right ends of the back part, respectively, to form a waist opening at upper ends of the front part and the back part and form a pair of leg openings under the front part and the back part, the pair of leg openings lying in left and right of the middle part; an absorbent body which is attached on the outer covering sheet to absorb excrement from the wearer, the absorbent body lying from the front part to the back part; and a sheet member which extends along an edge of upper end in one part of the front part and the back part and which is bonded on an inner surface of the outer covering sheet in the one part, one end portion of the absorbent body being fixed between the sheet member and the outer covering sheet; wherein the outer covering sheet and the sheet member are formed of nonwoven fabrics, a fiber orientation of nonwoven fabric in the sheet member is orthogonal to the edge of upper end. It is therefore possible to easily bring the absorbent body in close contact with the crotch region of the wearer when putting the disposable diaper on the wearer.

According to an aspect of the present invention, since a whole surface of the sheet member is bonded on the outer covering sheet and the absorbent body, it is easier to bring the absorbent body in close contact with the crotch region of the wearer.

According to another aspect of the present invention, the disposable diaper further comprises another sheet member having the same structure as the sheet member, wherein the sheet member and the other sheet member are provided to the front part and the back part, respectively. This makes it easier to bring the absorbent body in close contact with the crotch region of the wearer.

In this case, when the sheet member is distinguishable from the other sheet member, it is possible to easily recognize the front part and the back part of the disposable diaper.

These and other objects, features, aspects and advantages of the present invention will become more apparent from the following detailed description of the present invention when taken in conjunction with the accompanying drawings.

DETAILED DESCRIPTION OF THE INVENTION

Figure 1:
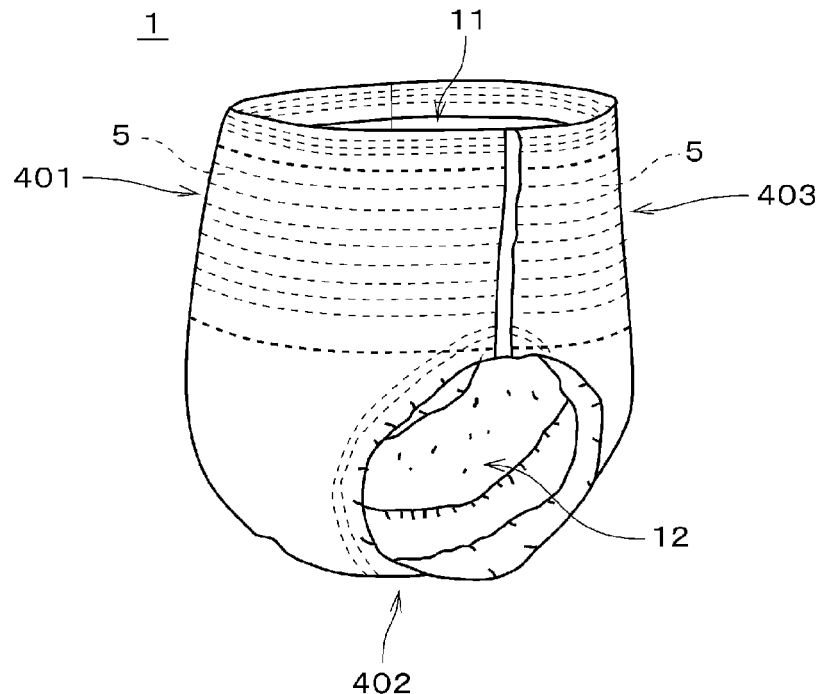
FIG. 1 is a perspective view showing an appearance of a disposable diaper in accordance with a first preferred embodiment.

FIG. 1 is a perspective view showing an appearance of a disposable diaper 1 in accordance with a first preferred embodiment of the present invention. As shown in FIG. 1, the disposable diaper 1 is a pants-type (i.e., pull-up type) diaper which has a waist opening 11 at an upper end, which is an end on the upper side of FIG. 1. The disposable diaper 1 has a pair of leg openings 12 on a lower part, and it receives excrement from a wearer.

Figure 2:
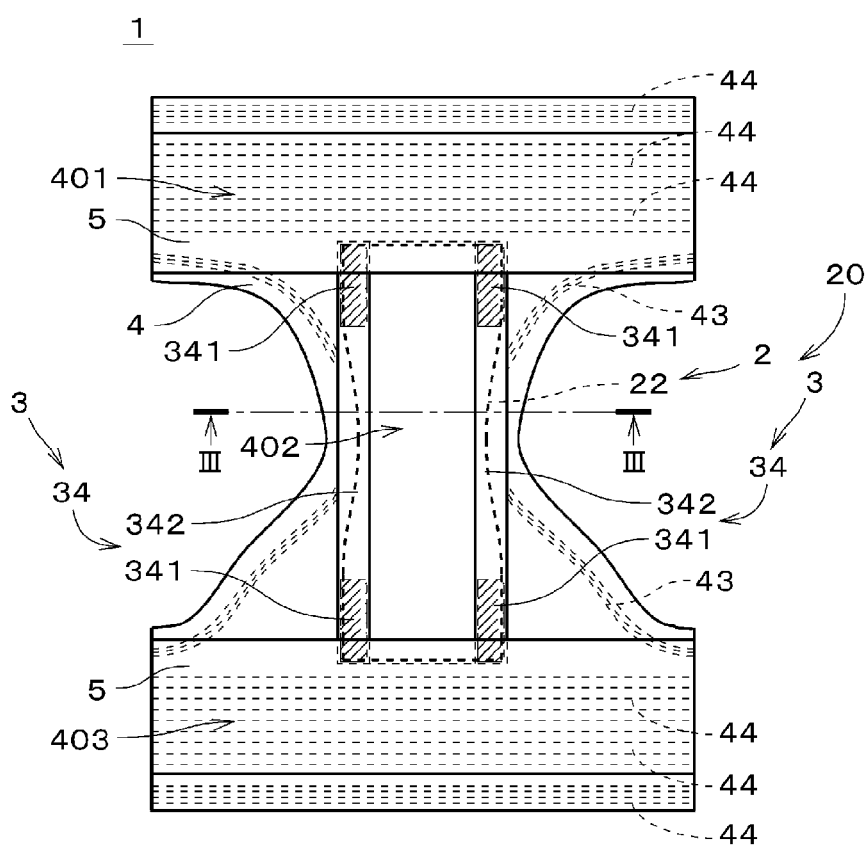
FIG. 2 is a plan view of the disposable diaper in a state where the disposable diaper is developed.

FIG. 2 is a plan view of the disposable diaper 1 in a state where the disposable diaper 1 is developed and in FIG. 2, the disposable diaper 1 is viewed from the wearer's side. As shown in FIG. 2, the disposable diaper 1 has an outer covering sheet 4, a sheet-like absorbent body (absorber) 20 which is attached on an inner surface (i.e., a surface to face the wearer) of the outer covering sheet 4 to absorb excrement from the wearer, and two sheet members 5 (they are also called as "end sheets" or "end holding sheets") which are bonded on the outer covering sheet 4 so as to cover both end portions of the absorbent body 20 in a longitudinal direction (i.e., an up-down direction in FIG. 2). Each sheet member 5 is provided across almost the entire width of the outer covering sheet 4 with respect to a left-right direction (lateral direction) in FIG. 2. Hereinafter, the left-right direction in FIG. 2 is referred to as a "width direction of diaper".

In the disposable diaper 1, an upper portion in FIG. 2 is to be positioned on (to cover) the front side (stomach side) of the wearer, and a lower portion in FIG. 2 is to be positioned on the back side of the wearer. In the following description, the portions of the disposable diaper 1 (and the portions of the outer covering sheet 4) to be positioned on the front side and the back side of the wearer are referred to as a "front part 401" and a "back part 403", respectively, and a portion to face the crotch region of the wearer at a position between the front part 401 and the back part 403 is referred to as a "middle part 402". The middle part 402 is continuous with both the front part 401 and the back part 403.

In manufacturing of the disposable diaper 1, the outer covering sheet 4 is folded at the middle part 402 together with the absorbent body 20. In the state where the middle part 402 is located on the downside, left and right ends of the front part 401 are bonded to left and right ends of the back part 403, respectively, by heat bonding (heat-sealing) under heating and pressing. As above, since both side ends of the front part 401 are bonded to both side ends of the back part 403, respectively, as shown in FIG. 1, the waist opening 11 is formed at upper ends of the front part 401 and the back part 403, and the pair of leg openings 12 lying left and right of the middle part 402 is formed under the front part 401 and the back part 403. Hereinafter, an up-down direction in FIG. 1 (the direction is not limited to the direction of gravity) is referred to as an "up-down direction of diaper".

Figure 3:
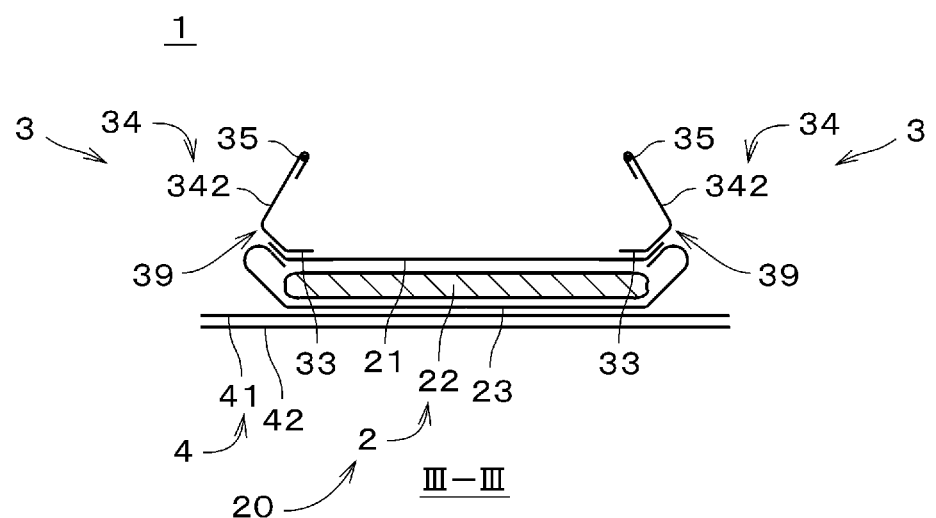
FIG. 3 is a cross-sectional view of the disposable diaper.

FIG. 3 is a cross-sectional view of the disposable diaper 1 taken along a line III-III in FIG. 2 (cross-sectioned at the middle part 402). In FIG. 3, respective constituents of the disposable diaper 1 are drawn so as to be slightly apart from one another for the convenience of illustration.

As shown in FIGS. 2 and 3, the absorbent body 20 has a sheet-like main body part 2 and a pair of side sheets 3 located on both side portions of the main body part 2 (i.e., both end portions of the main body part 2 in the width direction of diaper), and the pair of side sheets 3 extends across almost the entire length of the main body part 2 in the longitudinal direction. As shown in FIG. 3, the main body part 2 has a top sheet 21, a back sheet 23 and an absorbent core 22 which is located between the top sheet 21 and the back sheet 23. The back sheet 23 is bonded on the outer covering sheet 4 with hot melt adhesive or the like, to fix the absorbent body 20 on the outer covering sheet 4. The contour of the absorbent core 22 is drawn by thick broken lines in FIG. 2 for easy understanding of the drawing. As shown in FIG. 2, the width of the absorbent core 22 at each end portion in the longitudinal direction is larger than that at a middle portion in the longitudinal direction. In other words, the absorbent core 22 is formed in a form of hourglass.

As shown in FIG. 3, each side sheet 3 has a strip-like bonded part 33 and a side wall part 34. The bonded part 33 is one of two portions divided by a folding line 39 extending across almost the entire length thereof in the longitudinal direction and the bonded part 33 is positioned on the main body part 2. The side wall part 34 is the other of the two portions. The bonded part 33 is located in the vicinity of the side edge of the main body part 2, it lies across almost the entire length thereof in the longitudinal direction, and it is bonded on the upper side (i.e., the wearer's side) of the main body part 2 with hot melt adhesive.

The side wall part 34 is continuous from the bonded part 33 via the folding line 39. In both end portions thereof in the longitudinal direction, the side wall part 34 is laid on the bonded part 33 and fixed on the bonded part 33 by heat bonding, ultrasonic bonding or hot melt adhesive. In FIG. 2, hatching lines are drawn at each portion 341 of the side wall part 34 which is fixed on the bonded part 33, for easy understanding of the drawing. As shown in FIGS. 2 and 3, the side wall part 34 has a standing part 342 standing upward from the main body part 2 at a middle portion thereof in the longitudinal direction. In the side wall part 34 shown in FIG. 3, an elastic member 35 is bonded on a free edge of the standing part 342, and gathers are formed in the standing part 342 by contraction of the elastic member 35.

The outer covering sheet 4 has an inner sheet 41 and an outer sheet 42, and the outer sheet 42 is layered on the lower side (i.e., the side not to face the wearer) of the inner sheet 41. As shown in FIG. 2, a plurality of leg elastic members 43 and a plurality of waist elastic members 44 are bonded between the inner sheet 41 and the outer sheet 42 with hot melt adhesive or the like. In the disposable diaper 1, by contraction of the leg elastic members 43, the inner sheet 41 and the outer sheet 42 (see FIG. 3) are contracted and leg gathers are formed. Also by contraction of the waist elastic members 44, waist gathers are formed. Out of the plurality of waist elastic members 44, several waist elastic members 44 located in the vicinity of the edge of the waist opening 11 (see FIG. 1) are arranged densely, and the disposable diaper 1 fits around the wearer's waist tightly by these waist elastic members 44.

In each of the front part 401 and the back part 403 in FIG. 2, the above sheet member 5 is bonded on the outer covering sheet 4 (the inner sheet 41 of the outer covering sheet 4) with hot melt adhesive or the like. The sheet member 5 extends along the edge of the upper end of the disposable diaper 1 (i.e., the edge is edges of both end portions of the outer covering sheet 4 in the longitudinal direction). In the present embodiment, the sheet member 5 is a rectangle. When the sheet member 5 is bonded, hot melt adhesive is applied onto the whole area, to overlap with the sheet member 5, on the outer covering sheet 4 with a curtain spray gun or a coater, and therefore almost the whole area of the sheet member 5 is bonded on the inner surface of the outer covering sheet 4. Actually, the absorbent body 20 has been bonded on the outer covering sheet 4 while lying from the front part 401 to the back part 403. Thus, each end portion of the absorbent body 20 is positioned (sandwiched) between the sheet member 5 and the outer covering sheet 4, and therefore the absorbent body 20 is securely fixed on the outer covering sheet 4.

In the disposable diaper 1, a color of the sheet member 5 bonded on the front part 401 is different from a color of the sheet member 5 bonded on the back part 403. Since the outer covering sheet 4 is thin, the color of each sheet member 5 passes through the outer covering sheet 4 and is visually and easily recognizable when the disposable diaper 1 is observed from the outside.

The top sheet 21 is made of liquid-pervious sheet material, and the top sheet 21 immediately catches moisture of excrement from the wearer and moves the moisture into the absorbent core 22. For example, the top sheet 21 is a liquid-pervious nonwoven fabric made of hydrophobic fibers (polypropylene, polyethylene, polyester, polyamide, nylon or the like) where hydrophilic treatment is performed on its surface with a surfactant, and examples of nonwoven fabrics used for the top sheet 21 are a point-bond nonwoven fabric, air-through nonwoven fabric, and spunbond nonwoven fabric. A nonwoven fabric (for example, spunlace nonwoven fabric) made of hydrophilic fibers such as cellulose, rayon, cotton may be used as the top sheet 21.

The absorbent core 22 is formed by wrapping a mixture of hydrophilic fibers such as crushed pulp fibers or cellulose fibers and super absorbent material such as granulated super absorbent polymers (e.g., SAP (Super Absorbent Polymer)) or super absorbent fibers in a tissue paper, a liquid-pervious nonwoven fabric or the like, and the absorbent core 22 rapidly absorbs and retains the moisture which has passed through the top sheet 21. The tissue paper, the liquid-pervious nonwoven fabric or the like to wrap the hydrophilic fibers, is bonded to the hydrophilic fibers and the absorbent material with hot melt adhesive, to prevent deformation of the hydrophilic fibers and falling of the absorbent material (especially, falling after absorption of moisture). In the present embodiment, the absorbent core 22 includes pulp fibers and SAP.

As the back sheet 23, used is a water-repellent or liquid-impervious nonwoven fabric (for example, a spunbond nonwoven fabric, meltblown nonwoven fabric or SMS (spunbond-meltblown-spunbond) nonwoven fabric) made of hydrophobic fibers, or a water-repellent or liquid-impervious plastic film. The back sheet 23 prevents moisture of excrement or the like which has come to the back sheet 23, from leaking out to the outside of the main body part 2. In a case where a plastic film is used for the back sheet 23, it is preferable that a plastic film with permeability (breathability) is used, from the view point of preventing sweatiness in the disposable diaper 1 and providing comfortable feeling to the wearer.

As a sheet main body of the side sheet 3, used is a water-repellent or liquid-impervious nonwoven fabric (for example, a spunbond nonwoven fabric, meltblown nonwoven fabric or SMS nonwoven fabric) made of hydrophobic fibers. As the elastic member 35, for example, a polyurethane yarn, strip-like polyurethane film, yarn-like or strip-like natural rubber, or the like is used. In the present embodiment, a polyurethane yarn is used as the elastic member 35.

As the inner sheet 41 and the outer sheet 42 of the outer covering sheet 4, used is a water-repellent or liquid-impervious nonwoven fabric made of hydrophobic fibers in a similar fashion to the back sheet 23. In a similar fashion to the top sheet 21, a nonwoven fabric made of hydrophilic fibers or a liquid-pervious nonwoven fabric made of hydrophobic fibers where hydrophilic treatment is performed may be utilized as the inner sheet 41 and the outer sheet 42. As above, the outer covering sheet 4 is formed of a nonwoven fabric in the disposable diaper 1.

As the leg elastic members 43 and the waist elastic members 44, for example, a polyurethane yarn, strip-like polyurethane film, yarn-like or strip-like natural rubber, or the like is used in a similar fashion to the elastic member 35 of the side sheet 3. In the present embodiment, polyurethane yarns are utilized as the leg elastic members 43 and the waist elastic members 44.

Figure 4:
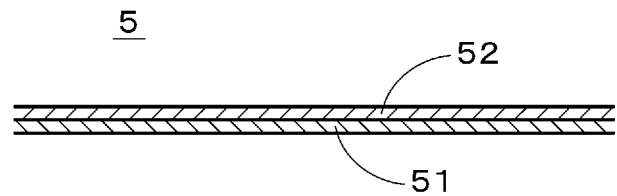
FIG. 4 is a cross-sectional view of a sheet member.

FIG. 4 is a cross-sectional view of the sheet member 5. The sheet member 5 is a laminated sheet (laminated body) containing a layer 51 formed of a plastic film and a layer 52 formed of a nonwoven fabric, and an inner surface of the sheet member 5 to face the wearer (i.e., a surface of the layer 52 which is not bonded on the outer covering sheet 4) is a surface of the nonwoven fabric. As the layer 52, used is a water-repellent or liquid-impervious nonwoven fabric made of hydrophobic fibers in a similar fashion to the outer covering sheet 4 and the back sheet 23, or a nonwoven fabric made of hydrophilic fibers or a liquid-pervious nonwoven fabric made of hydrophobic fibers where hydrophilic treatment is performed in a similar fashion to the top sheet 21. A water-repellent or liquid-impervious plastic film is used as the layer 51. It is preferable that a plastic film with permeability (breathability) is used.

When the disposable diaper 1 shown in FIG. 1 is put on a wearer, both legs of the wearer are inserted into the pair of leg openings 12 through the waist opening 11, and then the disposable diaper 1 is grabbed at edge portions around the waist opening 11 and pulled up so as to be around the waist of the wearer. At this time, the front part 401 is pulled upward (toward the head of the wearer) together with one sheet member 5, and the back part 403 is also pulled up together with the other sheet member 5. Therefore, each end portion of the absorbent body 20 is pulled upward so that the absorbent body 20 comes in close contact with the crotch region of the wearer.

Figure 5:
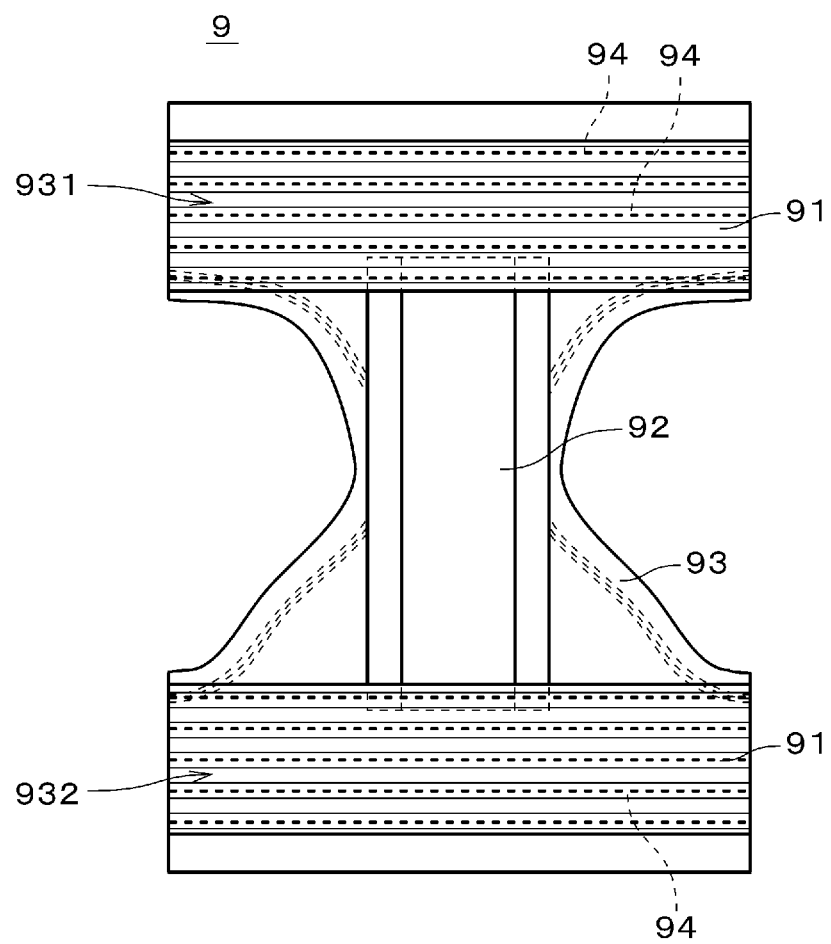
FIG. 5 is a view showing a disposable diaper in accordance with a comparative example.

FIG. 5 is a view showing a disposable diaper 9 in accordance with a comparative example, and FIG. 5 corresponds to FIG. 2. In the disposable diaper 9 of the comparative example, each sheet member 91 is formed of only a nonwoven fabric. On the other hand, in a nonwoven fabric roll used for manufacturing of the sheet member 91, a fiber orientation (i.e., the fiber orientation is a direction in which stiffness (strength needed to deform) of the nonwoven fabric is maximum, and also the fiber orientation is a direction in which stretchability is lowest) is identical to the withdrawing direction (i.e., sheet drawing direction), and a fiber orientation of nonwoven fabric in the sheet member 91 is parallel to the width direction of diaper (the left-right direction in FIG. 5) in order to simplify manufacturing of the disposable diaper 9 of the comparative example. In the nonwoven fabric, since stretchability is highest in a direction almost orthogonal to the fiber orientation, the sheet member 91 of the comparative example is easily stretched in the up-down direction of diaper which is orthogonal to the width direction of diaper. Parallel lines, each extending in the left-right direction, drawn at the sheet member 91 in FIG. 5 show that the fiber orientation of the nonwoven fabric which forms the sheet member 91 is parallel to the width direction of diaper. Actually, a fiber orientation of nonwoven fabric in the outer covering sheet 93 is also parallel to the width direction of diaper.

When bonding the sheet member 91 on the outer covering sheet 93, hot melt adhesive is applied on the outer covering sheet 93 in the form of a plurality of lines parallel to the width direction of diaper, as shown by thick broken lines denoted by reference signs 94 in FIG. 5, and then the sheet member 91 is laid and bonded on the outer covering sheet 93. In the above disposable diaper 9 of the comparative example, the sheet member 91 is easily stretched in the up-down direction of diaper together with the outer covering sheet 93. Thus, when the disposable diaper 9 is put on a wearer, even if the front part 931 and the back part 932 of the outer covering sheet 93 are pulled upward together with the sheet member 91 in order to bring the absorbent body 92 in close contact with the crotch region of the wearer, it is not easy to pull up the absorbent body 92 itself because of stretching of the outer covering sheet 93 and the sheet member 91. In addition, when moisture of excrement adheres to the inner surface of the sheet member 91, there may be a case where the moisture of excrement passes through the sheet member 91 and the outer covering sheet 93 by body pressure to leak out to the outside of the outer covering sheet 93.

Correspondingly, in the disposable diaper 1 of FIG. 2, since each sheet member 5 is the laminated sheet of the plastic film and the nonwoven fabric, stretching of the sheet member 5 is suppressed even if the fiber orientation of nonwoven fabric of the sheet member 5 is parallel to the width direction of diaper. It is therefore possible to surely pull up both end portions of the absorbent body 20 and to easily bring the absorbent body 20 in close contact with the crotch region of the wearer (i.e., to cause the both side ends of the absorbent body 20 to fit the groin of the wearer) when putting the disposable diaper 1 on the wearer. In addition, even when moisture of excrement adheres to the inner surface of the sheet member 5, it is possible to prevent the moisture of excrement from passing through the sheet member 5 to leak out to the outside of the outer covering sheet 4.

In the disposable diaper 1, the whole surface of the sheet member 5 is bonded on the outer covering sheet 4 (and the absorbent body 20) to unify the sheet member 5 and the outer covering sheet 4. This makes it more difficult to cause stretching of the sheet member 5, and it is easier to bring the absorbent body 20 in close contact with the crotch region of the wearer. Furthermore, since the color of the sheet member 5 positioned in the front part 401 is different from the color of the sheet member 5 positioned in the back part 403, it is possible to easily recognize the front part and the back part (the front and back) of the disposable diaper 1.

Figure 6:
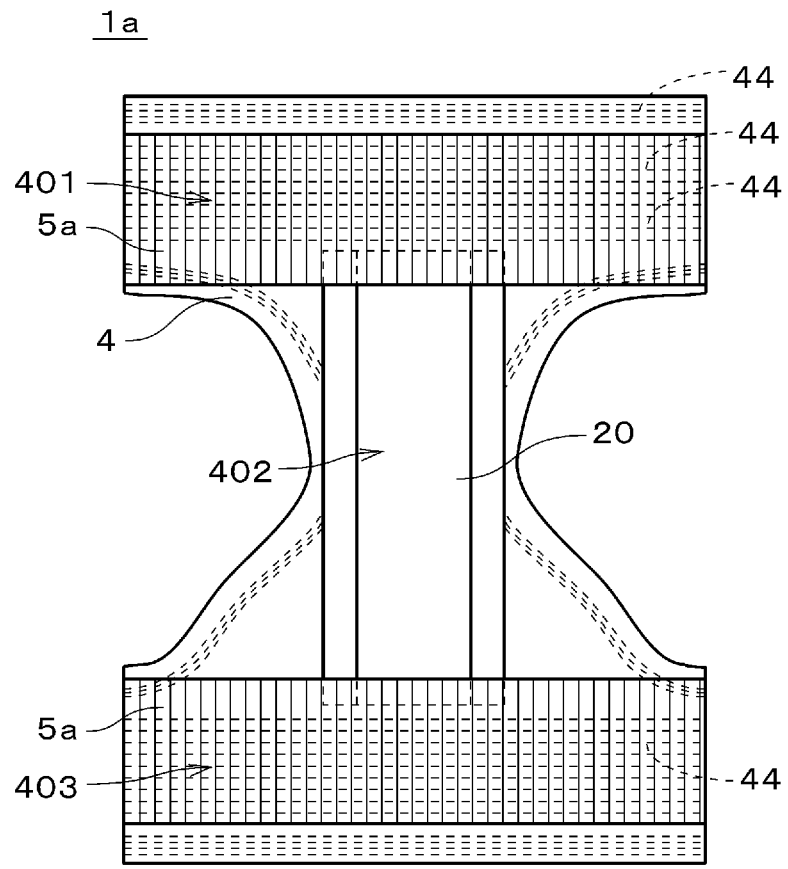
FIG. 6 is a plan view of a disposable diaper in accordance with a second preferred embodiment.

FIG. 6 is a view showing a disposable diaper 1*a* in accordance with a second preferred embodiment of the present invention, and FIG. 6 corresponds to FIG. 2. The disposable diaper 1*a* in FIG. 6 is different from the disposable diaper 1 in FIG. 2 in the point where the sheet member 5*a* is formed of only a nonwoven fabric. Constituent elements other than those are identical to those of the disposable diaper 1 in FIG. 2 and the same elements are denoted by the same reference signs.

In each sheet member 5*a* in FIG. 6, a fiber orientation of the nonwoven fabric is almost orthogonal to the waist elastic members 44, and stretchability of the sheet member 5*a* is highest in the width direction of diaper. In other words, the fiber orientation of the nonwoven fabric is parallel to the longitudinal direction of the absorbent body 20, and stretchability of the sheet member 5*a* is lowest in the up-down direction of diaper in the disposable diaper 1*a* where the left and right ends of the front part 401 are bonded to the left and right ends of the back part 403, respectively (see FIG. 1). Parallel lines, each extending in a vertical direction (up-down direction), drawn at the sheet member 5*a* in FIG. 6 show that the fiber orientation of the nonwoven fabric which forms the sheet member 5*a* is parallel to the longitudinal direction of the absorbent body 20.

Each sheet member 5*a* has a strip-like shape which extends along the edge of the end portion of the front part 401 or the back part 403 in a similar fashion to the sheet member 5 shown in FIG. 2, and the whole surface of the sheet member 5*a* is bonded to the inner surface of the outer covering sheet 4. In a similar fashion to the disposable diaper 1, a color of the sheet member 5*a* on the front part 401 is different from a color of the sheet member 5*a* on the back part 403. As above, the outer covering sheet 4 is formed of a nonwoven fabric.

Here, in the disposable diaper 9 of the comparative example shown in FIG. 5, since the fiber orientation of the nonwoven fabric in the sheet member 91 is parallel to the width direction of diaper, the sheet member 91 is easily stretched in the up-down direction of diaper and it is difficult to pull up the absorbent body 92 so as to bring the absorbent body 92 in close contact with the crotch region of the wearer, when putting the disposable diaper 9 on the wearer, as already described. In addition, since the sheet member 91 is hardly stretched in the width direction of diaper, there may be a case where the disposable diaper 9 does not fit (is not fastened) around the waist of the wearer appropriately.

Correspondingly, in the disposable diaper 1*a* shown in FIG. 6, since the fiber orientation of the nonwoven fabric in the sheet member 5*a* is orthogonal to the edge of the upper end of the disposable diaper 1 (i.e., the fiber orientation is along the up-down direction of diaper), the sheet member 5*a* is hardly stretched in the up-down direction of diaper (i.e., it is difficult to cause stretching of the sheet member 5*a* in the up-down direction of diaper). It is therefore possible to surely pull up the end portions of the absorbent body 20 and to easily bring the absorbent body 20 in close contact with the crotch region of the wearer when putting the disposable diaper 1*a* on the wearer.

In addition, along the fiber orientation of the nonwoven fabric in the sheet member 5*a*, the disposable diaper 1*a* is pulled up so as to be around the waist of the wearer, when putting the disposable diaper 1*a* on the wearer. Thus, feel of the disposable diaper 1*a* against skin of the wearer in pulling up the disposable diaper 1*a* can be improved when compared to the disposable diaper 9 of the comparative example. Furthermore, since stretchability of the sheet member 5*a* is highest in the width direction of diaper, the disposable diaper 1*a* can fit (can be fastened) around the waist of the wearer appropriately when compared to the disposable diaper 9 of the comparative example.

Though the preferred embodiments of the present invention have been discussed above, the present invention is not limited to the above-discussed preferred embodiments, but allows various variations.

In the disposable diaper 1, 1*a*, the sheet member 5, 5*a* may be provided on only one of the front part 401 and the back part 403. Also in this case, one end portion of the absorbent body 20 which is covered with the sheet member 5, 5*a* can be easily pulled up in the up-down direction of diaper, and it is possible to easily cause the absorbent body 20 to come in close contact with the crotch region of the wearer. In this case, there may be a case where the other end portion of the absorbent body 20 is covered with the sheet member 91 in the disposable diaper 9 of the comparative example or the other end portion is not covered with any sheet member. From the view point where the absorbent body 20 is more easily brought in close contact with the crotch region of the wearer, it is preferable that two sheet members having the same structure as each other are provided on the front part 401 and the back part 403, respectively.

Figure 7:
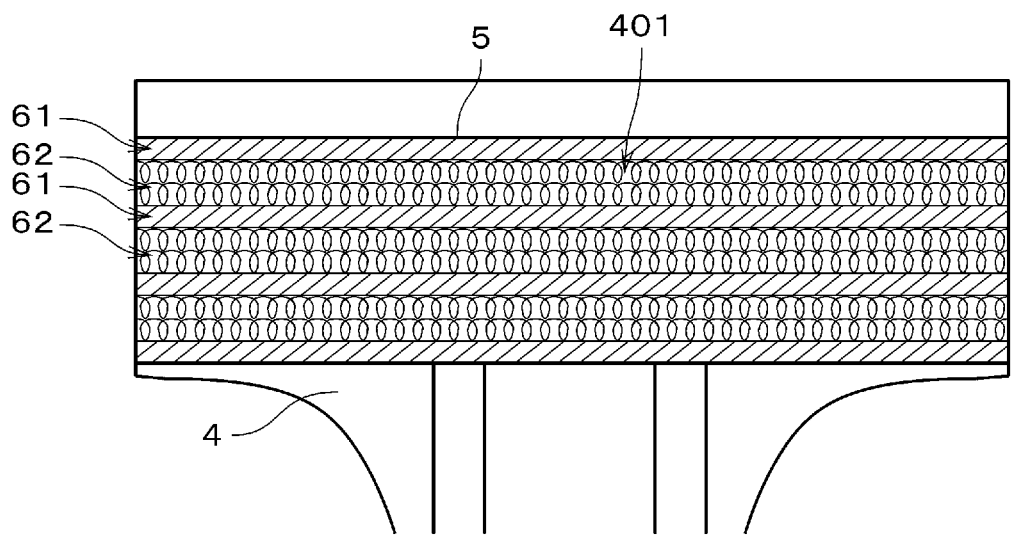
FIG. 7 is a view showing another example of disposable diaper.

In the above first and second preferred embodiments, the whole surface of each sheet member 5, 5*a* is bonded on the outer covering sheet 4 by application of hot melt adhesive with the use of a curtain spray gun or a coater. However, for example, as shown in FIG. 7, there may be a case where areas 61 in each of which hot melt adhesive is applied in a line (hatching lines are drawn at the areas in FIG. 7), and areas 62 in each of which hot melt adhesive is applied in spiral form are alternately provided in an up-down direction in FIG. 7 and almost the whole surface of the sheet member 5 is bonded on the outer covering sheet 4 (the same applies to the sheet member 5a). In each of the areas 62 in FIG. 7, hot melt adhesive is applied in two spiral rows extending in the width direction of diaper (it may be applied in one, three or more rows). In the above disposable diaper, breathability and softness around the waist of the wearer are improved. In a similar fashion to the disposable diaper 9 of the comparative example shown in FIG. 5, there may be a case where hot melt adhesive is applied on the outer covering sheet 4 so as to form a plurality of lines (or spiral rows) which are parallel to the width direction of diaper and which are arranged at intervals in the up-down direction of diaper, and therefore the sheet member 5, 5a is bonded on the inner surface of the outer covering sheet 4. Also in this case, the absorbent body 20 can be easily brought in close contact with the crotch region of the wearer by the sheet member 5, 5a which is hardly stretched in the up-down direction of diaper. In a certain design of disposable diaper 1, 1a, by applying hot melt adhesive on the outer covering sheet 4 so as to form a plurality of lines parallel to the longitudinal direction of the absorbent body 20, the sheet member 5, 5a may be bonded on the inner surface of the outer covering sheet 4.

In the above first and second preferred embodiments, since the color of the sheet member 5, 5a on the front part 401 is different from the color of the sheet member 5, 5a on the back part 403, the front part 401 and the back part 403 become distinguishable from each other in the disposable diaper. However, there may be a case where different characters, marks, patterns or the like are formed on the sheet member 5, 5a on the front part 401 and the sheet member 5, 5a on the back part 403, or a character(s), mark(s), pattern(s) or the like is formed on only one sheet member 5, 5a, and therefore the sheet member 5, 5a on the front part 401 becomes visually distinguishable from the sheet member 5, 5a on the back part 403.

The constituent elements of above-discussed preferred embodiments and modified examples may be appropriately combined with one another, as long as they are not mutually exclusive.

While the invention has been shown and described in detail, the foregoing description is in all aspects illustrative and not restrictive. It is therefore understood that numerous modifications and variations can be devised without departing from the scope of the invention.

REFERENCE SIGNS LIST 1, 1a disposable diaper
4 outer covering sheet
5, 5a sheet member
11 waist opening
12 leg opening
20 absorbent body
51, 52 layer
401 front part
402 middle part
403 back part

The invention claimed is:

1. A pants-type disposable diaper which has a waist opening at an upper end and a pair of leg openings on a lower part, comprising:
   an outer covering sheet which is folded in a middle part lying between a front part and a back part, said front part and said back part being adapted to be positioned on a front side and a back side of a wearer, left and right ends of said front part being bonded to left and right ends of said back part, respectively, to form a waist opening at upper ends of said front part and said back part and form a pair of leg openings under said front part and said back part, said pair of leg openings being located at left and right positions of said middle part;
   an absorbent body which is attached on said outer covering sheet to absorb excrement from the wearer, said absorbent body extending from said front part to said back part; and
   a first sheet member which extends along an edge of said upper end of one of said front part and said back part, said first sheet member being bonded on an inner surface of said outer covering sheet of said one part, one end portion of said absorbent body being fixed between said first sheet member and said outer covering sheet,
   wherein said outer covering sheet and said first sheet member are formed of nonwoven fabrics, and
   a fiber orientation of nonwoven fabric in said first sheet member is orthogonal to an edge of said waist opening.

2. The disposable diaper according to claim 1, wherein a whole surface of said sheet member is bonded to said outer covering sheet and said absorbent body.

3. The disposable diaper according to claim 2, further comprising a second sheet member having the same structure as said first sheet member, wherein said first sheet member and said second sheet member are bonded to said front part and said back part, respectively.

4. The disposable diaper according to claim 3, wherein said first sheet member is distinguishable from said second sheet member.

5. The disposable diaper according to claim 1, further comprising a second sheet member having the same structure as said first sheet member, wherein said first sheet member and said second sheet member are bonded to said front part and said back part, respectively.

6. The disposable diaper according to claim 5, wherein said first sheet member is distinguishable from said second sheet member.

* * * * *